United States Patent
Sanz Morales et al.

(10) Patent No.: US 8,329,877 B2
(45) Date of Patent: Dec. 11, 2012

(54) METHODS FOR SEPARATING RECOMBINANT PROTEINS IN AQUEOUS TWO-PHASE SYSTEMS

(75) Inventors: Jesús M. Sanz Morales, Seville (ES); Beatriz Maestro Garcia-Donas, Seville (ES); Miguel Arevalo Rodriguez, Seville (ES); Isabel Velasco Umpierrez, Seville (ES); Angel Cebolla Ramirez, Sevilla (JP)

(73) Assignee: Biomedal, S.L., Seville (ES)

( * ) Notice: Subject to any disclaimer, the term of this patent is extended or adjusted under 35 U.S.C. 154(b) by 144 days.

(21) Appl. No.: 12/723,356

(22) Filed: Mar. 12, 2010

(65) Prior Publication Data

US 2010/0234567 A1 Sep. 16, 2010

Related U.S. Application Data

(63) Continuation of application No. PCT/ES2008/000578, filed on Sep. 5, 2008.

(30) Foreign Application Priority Data

Sep. 12, 2007 (ES) .................. 200702504

(51) Int. Cl.
*A23J 1/00* (2006.01)
*C07K 1/00* (2006.01)
*C07K 14/00* (2006.01)
*C07K 16/00* (2006.01)
*C07K 17/00* (2006.01)

(52) U.S. Cl. ..................................... 530/412

(58) Field of Classification Search ................. None
See application file for complete search history.

(56) References Cited

U.S. PATENT DOCUMENTS 3,329,508 A * 7/1967 Freedman et al. ............ 426/548

FOREIGN PATENT DOCUMENTS

WO WO 00/058342 A1 10/2000

OTHER PUBLICATIONS

Caubin et al. Choline-Binding Domain as a Novel Affinity Tag for Purification of Fusion Proteins Produced in *Pichia pastoris*. Biotechnology and Bioengineering. 2001. vol. 74, Issue 2, pp. 164-171.*
Sanchez-Puelles et al. Searching for autolysin functions. Characterization of a pneumococcal mutant deleted in the lytA gene. Eur J Biochem. 1986, vol. 158, No. 2, pp. 289-293.*
De las Rivas. Purification and Polar Localization of Pneumococcal LytB, a Putative Endo-B-N-Acetylglucosaminidase: the Chain-Dispersing Murein Hydrolase. J. Bacteriol. 2002. vol. 184, Nol. 18, pp. 4988-5000.*
Koellner G. et al.; "A neutral molecule in a cation-binding site: specific binding of a PEG-SH to acetylcholinesterase from torpedo californica"; J.Mol.Biol., vol. 320; 2000; pp. 721-725.
Guan Y, et al.; "New approaches to aqueous polymer systems: theory, thermodynamics and applications to biomolecular separations"; Pure &Appl.Chem; vol. 67; No. 6; 1995; pp. 955-962.

* cited by examiner

*Primary Examiner* — Marcela M Cordero Garcia
(74) *Attorney, Agent, or Firm* — Arent Fox LLP (57) ABSTRACT

The object of the present invention is a procedure for the distribution, separation and purification in aqueous solution of recombinant proteins, based on the utilization of polypeptides with choline affinity. The invention is based on a phenomenon consisting of that two aqueous solutions with determinated components can be mixed, being distributed finally in two phases with different density. The fusionated proteins to said polypeptides with choline affinity are preferably located in one of the phases, while most of the cell extract proteins tend to go to the opposite phase. After a series of washings for removing the rest of the not desired material, this location can be inverted through the addition of a soluble molecule with affinity by the polypeptide fusionated to the protein of interest. This procedure allows modulating at convenience the presence of the protein or polypeptide of interest in one phase or another, possibiliting its purification with a high yield and purity grade. The invention represents an economic and scalable way of recombinant protein separation labelled preferably with choline-binding domains.

13 Claims, 8 Drawing Sheets

Figura 4

| Lysate Volumen | Purification Time | |
|---|---|---|
| | Resine (Max. flow 1 ml/min) | Two Phases (Centrifugation 5 min) |
| 10ml | 30-60min | 15-30min |
| 50ml | 1,5-2 h | 15-30min |
| 100ml | 3-4 h | 15-30min |
| 200ml | 6-7 h | 15-30min |

METHODS FOR SEPARATING RECOMBINANT PROTEINS IN AQUEOUS TWO-PHASE SYSTEMS

CROSS-REFERENCE TO RELATED APPLICATION

This application is a Continuation of International Application No. PCT/ES2008/000578, filed Sep. 5, 2008, which claims priority to Spanish Patent Application No. P200702504, filed Sep. 12, 2007. The disclosure of the prior application is hereby incorporated in its entirety by reference.

FIELD OF THE INVENTION

The present invention refers to a procedure for separating polypeptides or fusion proteins with a polypeptidic sequence of choline-binding, that presents moreover affinity for a water soluble polymer, and which determines an asymmetric distribution of the polypeptide or fusion protein in two-phase aqueous systems, one of which is rich in said polymer. The procedure allows a fast separation of the fusion protein from a complex protein mixture present in a cell extract, in a simple process that can use for the purification of the polypeptide or protein of interest. The purification process includes one or more washing steps and it completes with an inversion in the distribution of the fusion protein induced by the addition at the system of the natural ligand of the affinity polypeptide. The field of the invention at which can be applied this invention comprises therefore the production, separation and eventual purification of polypeptides and proteins of biotechnologic interest, as well as being with industrials, agronomics, therapeutics or of diagnostic purposes in biomedicine, or as a research tool and analysis in the field of the life sciences.

STATE OF THE ART

The immobilization of enzymes in solid supports is an usual procedure as for proceeding to its purification through chromatographic techniques as for the construction of enzymatic reactors for carrying out all type of biotransformations (Mosbach, K., ed. *Immobilized Enzymes and Cells Part B. Methods in Enzymology.* Vol. 135. 1987). For it, it has been developed a large variety of immobilization systems as covalent as non covalent. In determinated cases, it is useful to use a fusion of the protein of interest with a affinity polypeptide or "tag" that makes possible a strong and specific interaction with the solid support (Uhlen, M., et al., Fusion proteins in biotechnology. *Curr Opin Biotechnol,* 1992. 3(4): p. 363-9; Waugh, D. S., Making the most of affinity tags. *Trends Biotechnol,* 2005. 23(6): p. 316-20). However, very often the enzymes immobilization in solid matrixes causes a change of the protein characteristics, as structural as functional level. Thus, for example, the physical-chemical peculiarities of the support can influence in the substrate diffusion to the enzymatic phase, or of the product to the mobile phase, causing a change in the kinetic constants of the enzyme that in many times it is translated in the process efficiency reduction and, in any case, in the need of doing expensive studies of setting up. On the other hand, the scaled of the chromatographic methods for its industrial use, entails a series of technical difficulties that result basically of the materials compressibility and the need of applying high pressions in column. For this reason, recently it is being developed new methods in solution that represent an alternative at the use of solid materials. In this sense, the aqueous two-phase systems are generated spontaneously by the mixture of certain solutions of two polymers structurally different, or by the mixture of a polymer (usually polyethylenglycol or PEG) and high concentrations of a salt (Johansson, H. W. a. G., ed. *Aqueous Two-Phase Systems. Methods in Enzymology.* Vol. 228. aquas, New approaches to aqueous polymer systems: Theory, thermodynamics and applications to bimolecular separations. *Pure and Applied Chemistry,* 1995. 67(6): p. 955-962; Andrews, B. A., A. S. Schmidt, and J. A. *aqueos Biotechnol Bioeng,* 2005. 90(3): p. 380-90). After a short period two phases appear, both aqueous, and that they are found in equilibrium. In two polymer mixtures, each phase is enriched in one of the two polymers, while in polymer-salt systems one phase is enriched in polymer, and the other in salt. The chemical-physical properties of these mixtures have been largely studied (Cahezas, H., Jr., Theory of phase formation in aqueous two-phase systems. *J Chromatogr B Biomed Appl,* 1996. 680(1-2): p. 3-30) and it has been built binodal diagrams that showed the concentration ranges of each one of the compounds that provoke to the phase separation. The lines denominated "tie lines" indicate the final concentrations of each polymer in each phase, once separate them, thus as the relative volumes of each one of the phases (Johansson, H. W. a. G., ed. *Aqueous Two-Phase Systems. Methods in Enzymology.* Vol. 228. 1994). The aqueous two-phase systems have a great utility in the biological material separation (Hustedt, H., K. H. Kroner, and M. R. Kula, Applications of phase partitioning in biotechnology, in *Partitioning in Aqueous two-phase systems: theory, methods uses and applications in biotechology,* H. Walter, D. E. Brooks, and D. Fisher, Editors. 1985, Academic Press: Orlando, Fla., p. 529-587; Persson, J., et al., Purification of recombinant and human apolipoprotein A-1 using surfactant micelles in aqueous two-phase systems: recycling of thermoseparating polymer and surfactant with temperature-induced phase separation. *Biotechnol Bioeng,* 1999. 65(4): p. 371-81). They have several advantages, such as the high biocompatibility, low surface tension (it minimizes the biomolecules degradation), high capacity of charge and yield, and they are easily scalable (Albertsson, P. A., *Partition of cell particles and macromolecules.* 1986, New York: Wiley; Walter, H., G. Johansson, and D. E. Brooks, Partitioning in aqueous two-phase systems: recent results. *Anal Biochem,* 1991. 197(1): p. 1-18). In enzymatic catalysis process, the mass transfer (substrates and products) between the enzymatic phase and the rest, it is much more facilitated than when the enzyme is adsorbed on a solid surface. Furthermore, they are economic systems, and in which can be managed many factors for arising improve the partition of the molecules of interest. The proteins distribution between the two phases is dependent on factors such as the charge, the size and the hydrophobicity of the protein in question, and it is a question in general poorly predictable. In fact, the major establishment in the market of these systems comes limited by the low predictability in the proteins partition. However, the use of affinity polypeptides or "tags" fusionated to the protein of interest can induce at their location in one or another phase in a more controlled way, it is denominated partition by affinity in aqueous two-phase systems. It has been described promising results using the known hexahystidine "tag" (Chung, B. H., D. Bailey, and F. H. Arnold, Metal affinity partitioning, in *Aqueous Two-Phase Systems,* H. W. a. G. Johansson, Editor. 1994. p. 167-277; Birkenmeier, G., et al., Immobilized metal ion affinity partitioning, a method combining metal-protein interaction and partitioning of proteins in aqueous two-phase systems. *J Chromatogr,* 1991. 539(2): p. 267-77). In this system, the fusion protein to the tail of hystidines is managed in a majority way to the rich phase in PEG, that has previously been derivatized in a covalent way with metallic ions. Likewise, it has also been studied the tyrosine sequences (Fexby, S., et al., Partitioning and characterization of tyrosine-tagged green fluorescent proteins in aqueous two-phase systems. *Biotechnol Prog*, 2004. 20(3): p. 793-8) or of triptophanes (Cohen, A., et al., Genetic engineering of the *Trichoderma reesei* endoglucanase I (Cel7B) for enhanced partitioning in aqueous two-phase systems containing thermoseparating ethylene oxide—propylene oxide copolymers. *J Biotechnol*, 2001. 87(2): p. 179-91) in such partitioning procedures by affinity.

The choline-binding modules (CBM, "choline-binding modules") constitute a polypeptides family that become part of the named choline-binding proteins (CBP, "choline-binding proteins), present in a variety of microorganisms (Swiatlo, E. and e. al., Choline-binding proteins, in *The Pneumococcus*, E. I. Tuomanen, T. J. Mitchell, and D. A. Morrison, Editors. 2004, American Society for Microbiology: Washington, D.C. p. 49-60). The CBMs consist, in their turn, of the sequences repetition very preserved of approximately 20 aminoacids (CBR o "choline-binding repeats"; code Pfam PF01473: http://www.sanger.ac.uk//cgi-bin/Pfam/getac-c?PF01473), that form structures of the type loop-fold-β (Fernandez-Tornero, C., et al., A novel solenoid fold in the cell wall anchoring domain of the pneumococcal virulence factor LytA. *Nat Struct Biol*, 2001. 8(12): p. 1020-4; Hermoso, J. A., et al., Insights into pneumococcal pathogenesis from the crystal structure of the modular teichoic acid phosphorylcholine esterase Pee. *Nat. Struct Mol Biol*, 2005. 12(6): p. 533-8; Hermoso, J. A., et al., Structural basis for selective recognition of pneumococcal cell wall by modular endolysin from phage Cp-1. *Structure*, 2003. 11(10): p. 1239-49). Two consecutive CBRs configure a binding site of choline. The affinity of the CBMs to choline and structural analogous of the same (Sanz, J. M., R. Lopez, and J. L. Garcia, Structural requirements of choline derivatives for 'conversion' of pneumococcal amidase. A new single-step procedure for purification of this autolysin. *FEBS Lett*, 1988. 232(2): p. 308-12), has allowed to set-up an effective system of fusion proteins purification with some of these CBMs (Sanchez-Puelles, J. M., et al., Immobilization and single-step purification of fusion proteins using DEAE-cellulose. *Eur J Biochem*, 1992. 203(1-2): p. 153-9). Basically, the procedure consists on applying a cell extract containing the fusion protein on a derivatized support with tertiary or quaternary amines as the diethylaminoethanol (DEAF). The protein thus immobilized, maintains its functionality, and can be easily eluted through the addition of a competitor ligand, as the choline. The procedure thus described is the base of two previous patents (ES 2 032 717 y ES200700281) in which has been used of the C-terminal domain of the amidase LytA, and is denominated LYTAG. Among the advantages of this procedure, it is worth mentioning that the system protocol for the partitioning of polypeptides and proteins, fused to the LYTAG module, in aqueous two-phase systems, said partitioning being modulated by the addition of choline. This invention expands the applications of the LYTAG module, from its current configuration as an affinity tag in solid phase affinity chromatography, to its use in affinity partitioning in aqueous two-phase systems. Furthermore, the procedure can employ any choline-binding module of the same structural family than LYTAG.

BRIEF DESCRIPTION OF THE INVENTION

The object of the present invention is a procedure for solution partitioning and purification of polypeptides and proteins fused to choline-binding polypeptidic modules, based on the use of binary aqueous systems in which the main compounds are distributed spontaneously in two phases, one of them rich in a soluble polymer with affinity to choline-binding modules (CBMs) and the other one enriched in a different polymer or in a salt. The procedure follows the scheme showed in FIG. 3, and it consists basically in the incubation of an aqueous extract, obtained from a cell culture that expresses a fusion of the protein of interest with a choline-binding module (CBM) containing at least one choline-binding repeat (CBR), with the binary system components in the appropriate concentrations and proportions for favouring the separation of the mixture in two differentiated phases. As a result of the CBM affinity to the above mentioned polymer, the fusion protein is located after phase separation preferably in the phase rich in this polymer, so that it is possible to remove the opposite phase, and concomitantly, the other proteins and cellular components from the extract that have partitioned to it. The discarded phase is then substituted with an equivalent volume of a fresh solution with the same original composition, and the system is mixed and then allowed to settle for phase separation, before discarding the same phase as in the previous step. This washing procedure is repeated as many times as needed, until the removed phase presents a minimum quantity of contaminant proteins. At this point, the discarded phase is replaced with an equivalent volume of a solution with the same original composition, this time containing choline at a concentration that has the effect of reverting the binding of the CBM-tagged protein to the polymer, competing with this polymer for the binding to the protein and specifically displacing it to the opposite phase, from where it can be finally recovered with a high purity grade.

The procedure object of the present invention comprises preferably the use of PEG (3-15%) and potassium phosphate (5-15%), for example at 15% and 12.5%, respectively. In another preferred configuration potassium phosphate can be substituted with another, highly soluble phosphate, sulphate or citrate salt, which is compatible with formation of the two-phase system. The PEG molecular weight useful in this system ranges from PEG-6000 to PEG-20000, being the preferred configuration the one that uses PEG-8000 (henceforth, PEG).

The procedure object of the present invention comprises preferably the use of PEG (3-15%) and potassium phosphate (5-15%), for example at 15% and 12.5%, respectively. In another preferential configuration could be substituted the potassium phosphate by other phosphate, sulphate or citrate salts, that also have high solubility in water and would allow the separation of two phases. The molecular weight range of the PEG that have been proved with successful includes from PEG-6000 until PEG-20000, being the preferential configuration the one that uses PEG-8000 (later on, it will simply mention as PEG).

It exists another preferential configuration that comprises two phases conformed through the use of solutions with PEG (3-15%) and dextran (5-10%, for example at 6%) and can allow the phases separation in 20 mM Tris-HCl buffer pH 8.0. In another preferential configuration, the dextran can be replaced by derivatives substituted of the same or by polysaccharides of similar structure as the starch and their derivatives.

Figure 1:
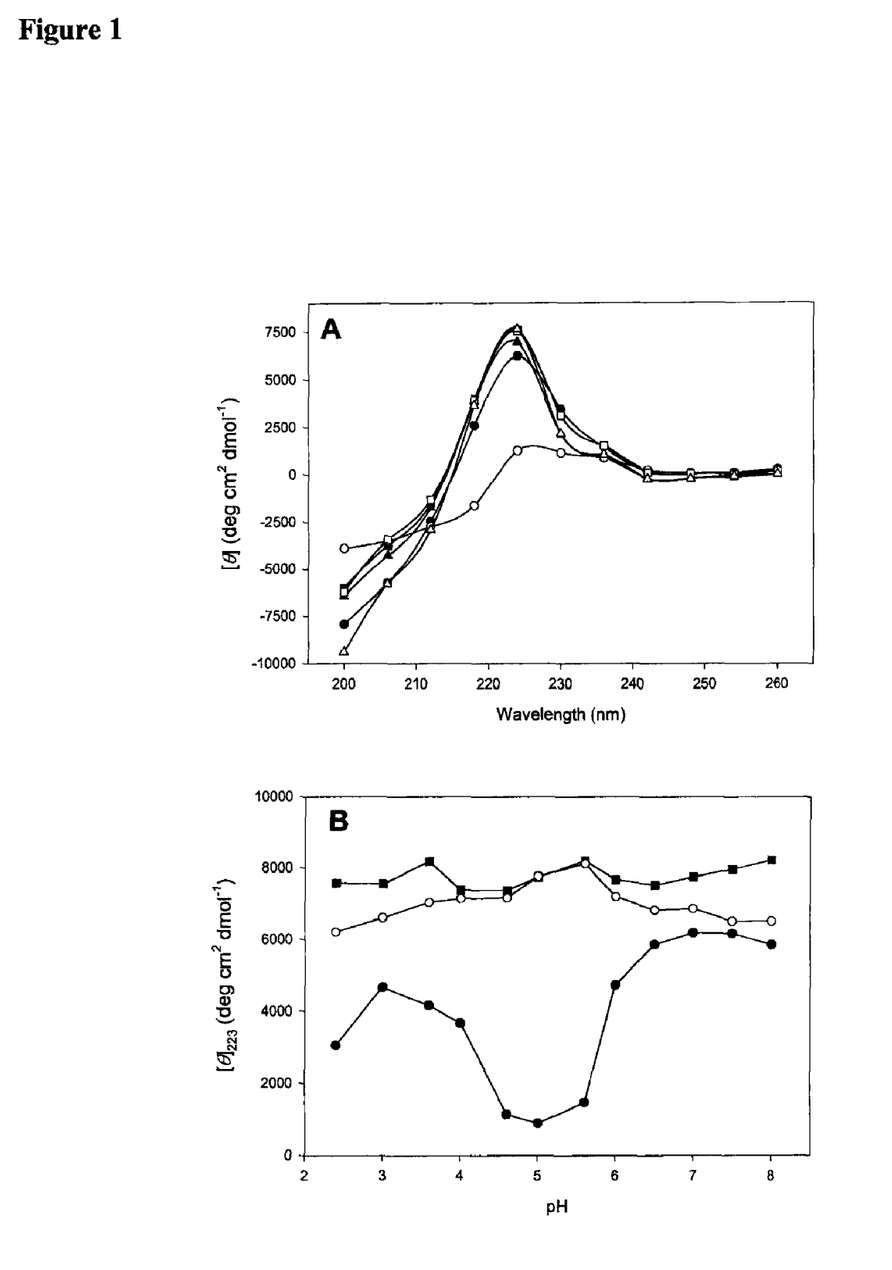
FIG. 1. CD analysis in the far ultraviolet of the pH effect over the LYTAG structure at 20° C. (A), wavelength spectra registered at pH 7.0 (solid symbols) and pH 5 (open symbols) in the absence of additives (circles), in the presence of 10% PEG (triangles) or in the presence of 140 mM choline (squares). (B), pH titration followed by the CD signal at 223 nm in the absence of additives (filled circles), in presence of 140 mM choline (squares) and in presence of 10% PEG (open circles).
Figure 2:
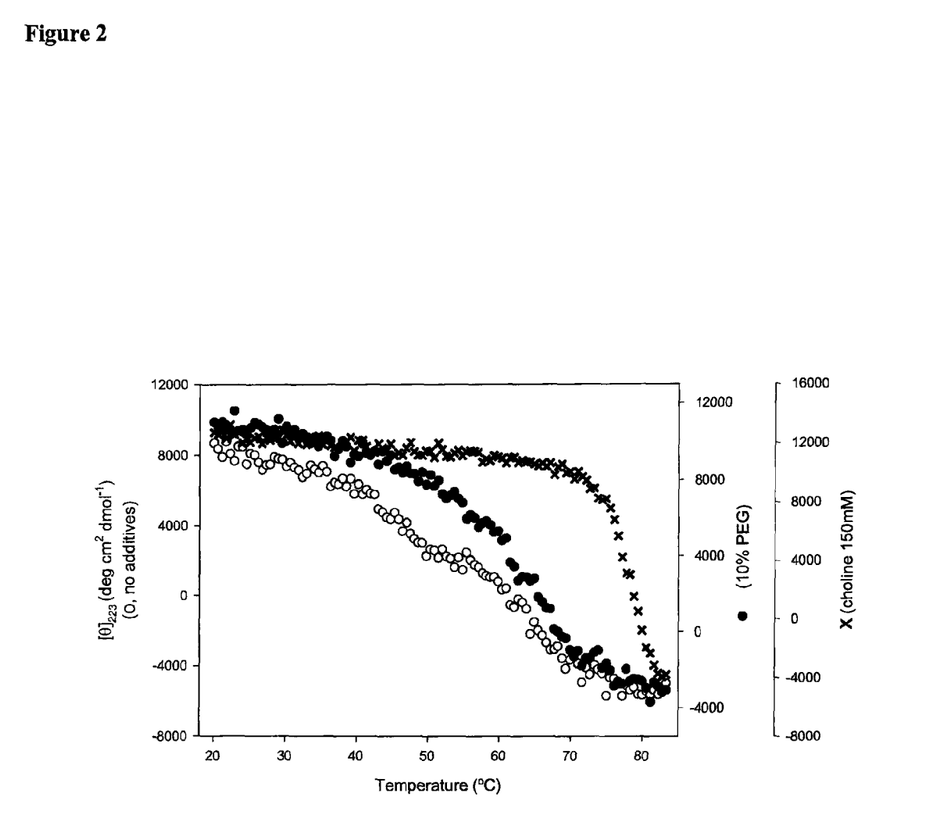
FIG. 2: Thermal stability of LYTAG followed by circular dichroism in the absence of additives (o), in presence of 10% PEG (●) and the presence of 150 mM choline (x).

According to the chosen system, the cells from the microbial culture are collected by centrifugation and they are resuspended preferably in 20 mM potassium phosphate buffer pH 8.0, in the case of that the purification is carried out in the system PEG/Phosphate, or in 20 mM Tris-HCl buffer pH 8.0 in the case of the system PEG/Dextran. After lysing the cells through sonication, it is centrifuged the resulting crude extract for removing the cellular rests, and at the supernatant obtained is added the needed quantity of PEG and dipotassium phosphate, or of PEG and dextran, until reaching the concentrations and proportions described for each system. The solution thus obtained is softly shaked during a short time, passed which it is allowed its separation in two phases, that can be accelerated through centrifugation of the mixture. Before doing the next steps, it can be verified the presence of fusion proteins at the CBD in the upper phase, corresponding to the phase rich in PEG in both systems described through electrophoretic analysis in polyacrilamide gels (SDS-PAGE), for example, or by immunological methods using antibodies that recognize the choline-binding domain. Next, it is proceeded to remove the inferior phase rich in phosphate or in dextran, according to the used system, using a pipette or a decantation funnel, after which, it is added to the mixture a volume, equal to the removed phase, which concentration depends on the binodale diagram of the system in question (Johansson, H. W. a. G., ed. *Aqueous Two-Phase Systems. Methods in Enzymology*. Vol. 228. 1994) and on the initial concentrations of the used reagents, with the object of preserving the phase separation and their relative volumes. After repeating several times this washing process, it can be chosen for using the upper phase, enriched in the protein of interest, or else include a last step in which the lower phase is replaced by a solution of the same composition, but containing choline. Once mixed the solution and formed newly the two characteristic phases of the system, the fusion protein to CBD will be located preferably in the lower phase, in a high purity grade. The invention described microorganisms (patent ES2032717; Swiatlo, E. et. al., Choline-binding proteins, in *The Pneumococcus*, E. I. Tuomanen, T. J. Mitchell, and D. A. Morrison, Editors. 2004, American Society for Microbiology: Washington, D.C. p. 49-60), contain structural repeats with natural affinity to choline. The present invention exploits this specific interaction between PEG and these CBMs. This interaction can be revealed by circular dichroism analysis of the LYTAG module (a C-LytA derivative) in the presence of the polymer. In aqueous medium at pH 7 and the absence of choline the LYTAG protein is found partly denatured (Maestro, B. and J. M. Sanz, Accumulation of partly folded states in the equilibrium unfolding of the pneumococcal choline-binding module C-LytA. *Biochem J,* 2005. 387(Pt 2): p. 479-88) and as a result, its circular dichroism spectrum is poorly reproducible, and highly affected by sample storing conditions, including the freezing-thawing cycles suffered during the assays. However, addition of choline stabilizes the LYTAG protein, increasing its ellipticity (FIG. 1A). According to the LYTAG choline binding structure (Fernandez-Tornero, C., et al., A novel solenoid fold in the cell wall anchoring domain of the pneumococcal virulence factor LytA. *Nat Struct Biol,* 2001. 8(12): p. 1020-4), this amino alcohol seems to play an essential role in the protection of the hydrophobic zones present in the choline-binding sites, and in inducing dimerization through the last fork, resulting in a significant increase in protein stability (Fernandez-Tornero C., et al., A novel solenoid fold in the cell wall anchoring domain of the pneumococcal virulence factor LytA. *Nat Struct Biol,* 2001. 8(12): p. 1020-4; Usobiaga, P., et al., Structural organization of the major autolysin from *Streptococcus pneumoniae. J Biol Chem,* 1996. 271(12): p. 6832-8). Addition of 10% PEG produces a stabilizing effect on the circular dichroism spectrum similar to that induced by a high concentration of choline (FIG. 1A), indicating that both PEG and choline share interaction sites in LYTAG. On the other hand, the solubility of a given protein exhibits a minimum around the pH value corresponding to its isoelectric point, as the absence of a net electric charge favours the intermolecular aggregation mediated by interactions of the hydrophobic type. In this sense, the binding of a ligand to its cognate protein can contribute to hide hydrophobic regions present in it, thus increasing its solubility at pH values close to its isoelectric point. As shown in FIG. 1B, the circular dichroism signal at 223 nm in a preparation of the LYTAG protein remains unaltered in the range of pH values between 6.5 and 8.0, and it decreases below pH 6.0, with a minimum between pH 4.5 and pH 5.5. At pH 5.0 the spectrum shows a general decrease of the signal at all wavelengths (FIG. 1A), and a reduction of the sample absorbance is detected (data not shown). This suggests that the solubility of LYTAG has a minimum in this pH range, resulting in protein aggregation and decreasing this way the population of soluble molecules susceptible to produce a circular dichroism signal. These results agree with the expected according with the theoretical isoelectric point of the protein, 5.3, obtained with a software application (http://www.embl-heidelberg.de/cgi/pi-wrapper.pl). Addition of choline at a saturating concentration (140 mM) induces a general increase of the ellipticity and stabilizes the LYTAG protein in the range of pH values between 2.4 and 8.0 (FIGS. 1A and 1B), supporting the hypothesis that binding of this ligand results in the hiding of hydrophobic sites that would be otherwise exposed, thus preventing protein aggregation. Also in support to this hypothesis, addition of low polarity additives such as 2% CHAPS or 140 mM 2,2-dimethylpropanol (DMP) also recover the circular dichroism spectrum at pH 5.0 (data not shown). When these assays are performed in the presence of 10% PEG, the results are similar to those obtained with choline (FIGS. 1A and 1B), reinforcing the hypothesis that this polymer interacts with the LYTAG protein, producing an effect that is similar to that produced by the binding of its natural ligand indicating that both PEG and choline interact with the same protein region. This is also indicated by the fact of that the LYTAG protein loses its capacity of being retained in a DEAF-cellulose column in the presence of PEG (data not shown), indicating that the PEG intercalates into the choline-binding sites, preventing further binding of the CBM to DEAF. Finally, it has also been shown that PEG could be emulating the stabilizing effect of choline over the LYTAG structure, by studying the thermal stability of the protein through circular dichroism analysis at 223 nm (FIG. 2). In the absence of a ligand, LYTAG is displays a biphasic transition originated by the accumulation of an intermediate state (Maestro, B. and J. M. Sanz, Accumulation of partly folded states in the equilibrium unfolding of the pneumococcal choline-binding module C-LytA. *Biochem J,* 2005. 387(Pt 2): p. 479-88). The presence of 150 mM choline prevents accumulation of such intermediate state, generating a unique sigmoidal curve as well as thermal stabilization, as described previously (Maestro, B. and J. M. Sanz, Accumulation of partly folded states in the equilibrium unfolding of the pneumococcal choline-binding module C-LytA. *Biochem J,* 2005. 387(Pt 2): p. 479-88). In similar assays carried out in the presence of PEG, results showed that addition of this compound causes an intermediate effect, preventing accumulation of the intermediate state without affecting the denaturalization temperature (FIG. 2). Taken together the studies described establish the affinity of the CBMs to PEG as one of the bases of the present invention.

General Protocol of Purification by Affinity of Fusions to LYTAG in Aqueous Two-Phase Systems The present invention is based on the results previously described, indicating interaction between LYTAG and PEG, and provides realization examples in which this polymer has been used in protein separation using two-phase aqueous systems, allowing the development of separation protocols for polypeptides and proteins fused with choline-binding modules.

In a preferred protocol, PEG/phosphate and PEG/dextran combinations are used in the two-phase aqueous systems used in the separation procedure. The PEG/phosphate system is formed at different concentration ranges of PEG (3-15%) and potassium phosphate (5-15%) at pH 8.0, with the preferred 15% PEG/12.5% phosphate combination, pH 8.0 (henceforth, ExtP buffer) showing the smallest volume difference between the PEG-rich (upper) phase and the phosphate-rich (lower) phase. On the other hand, the PEG/dextran system is formed at different concentration ranges of PEG (3-10%) and dextran (5-10%), with the preferred 6% PEG system/6% dextran combination, in 20 mM Tris-HCl buffer pH 8.0 (henceforth ExtD buffer), also showing the smallest volume difference between the PEG-rich (upper) phase and the dextran-rich (lower) phase.

Figure 3:
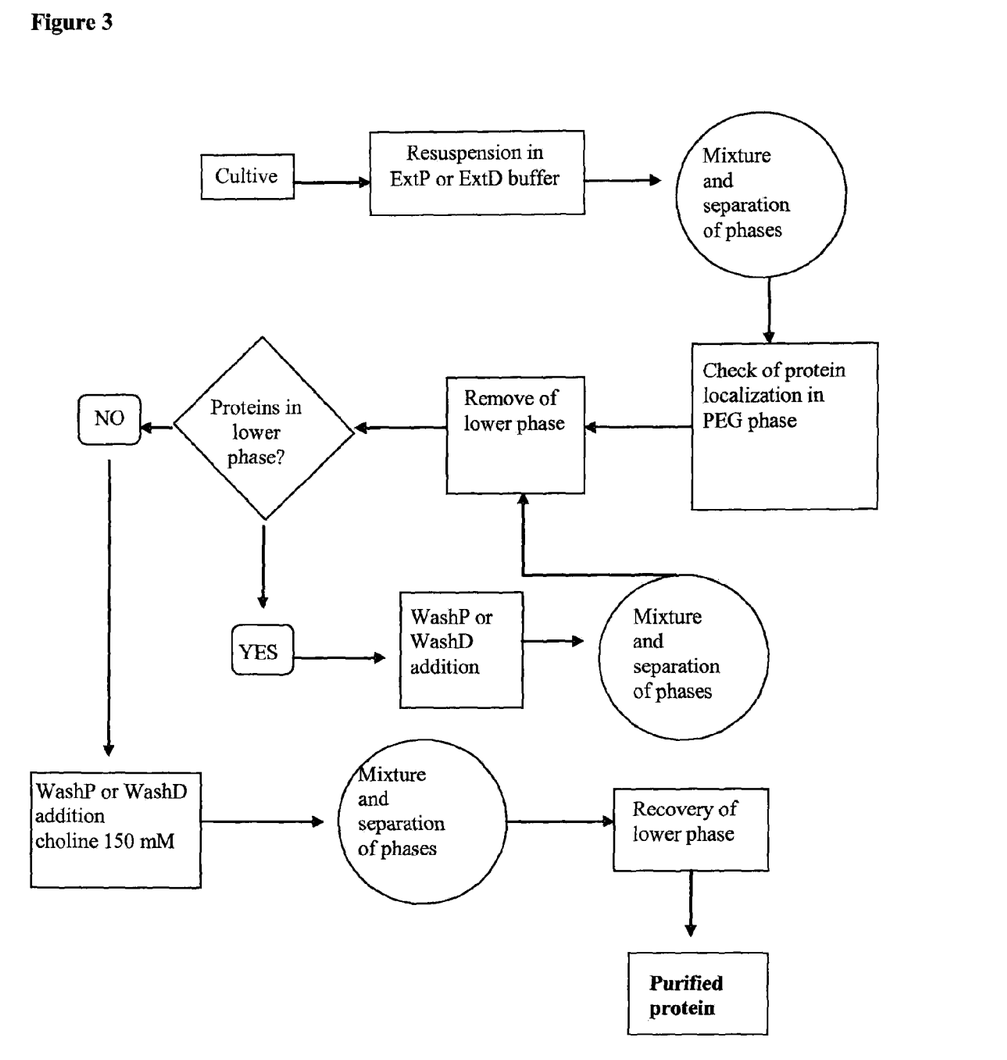
FIG. 3. Purification of LYTAG-fused proteins by affinity partitioning.

The general protocol is summarized in FIG. 3 and starts by obtaining a cell extract expressing a polypeptide or protein of interest as a fusion with a CBM containing at least one CBR, in a preferred case, the LYTAG. Said extract is mixed with the compounds required for the generation of the two-phase system, and the phases allowed to separate by centrifugation, or by gravity. The LYTAG affinity to PEG described before determines the quantitative partitioning of the LYTAG fusion to the upper phase containing this polymer (see detailed examples below). Once verified the accumulation of the LYTAG fusion in the upper phase, a series of washing steps can be applied consisting in removing the lower phase and replacing it with the same volume and composition of the discarded one. Based on the data from the binodal diagrams published in the literature (Johansson, H. W. a. G., ed. *Aqueous Two-Phase Systems. Methods in Enzymology*. Vol. 228. 1994), and in the cases of the preferred configurations mentioned above, the composition of this fresh phase consists of 1% PEG, 16% potassium phosphate, pH 8.0 (henceforth, WashP buffer) or 0.5% PEG, 16% dextran in Tris-HCl 20 mM pH 8.0 (henceforth, WashD buffer). After a new mixing and phase separation process, the lower phase is replaced with WashP, or with WashD buffer, and the process is repeated 2-3 times. At this point, the purity of the protein of interest in the PEG phase can already be sufficiently high. However, inclusion of 150 mM choline in the WashP or the WashD buffers has the effect of displacing the PEG from the ligand-binding sites of the fusion protein, disrupting its interaction with the polymer and hence allowing recovering of the fusion protein in the lower phase, which can thus be purified to electrophoretic homogeneity.

Figure 4:
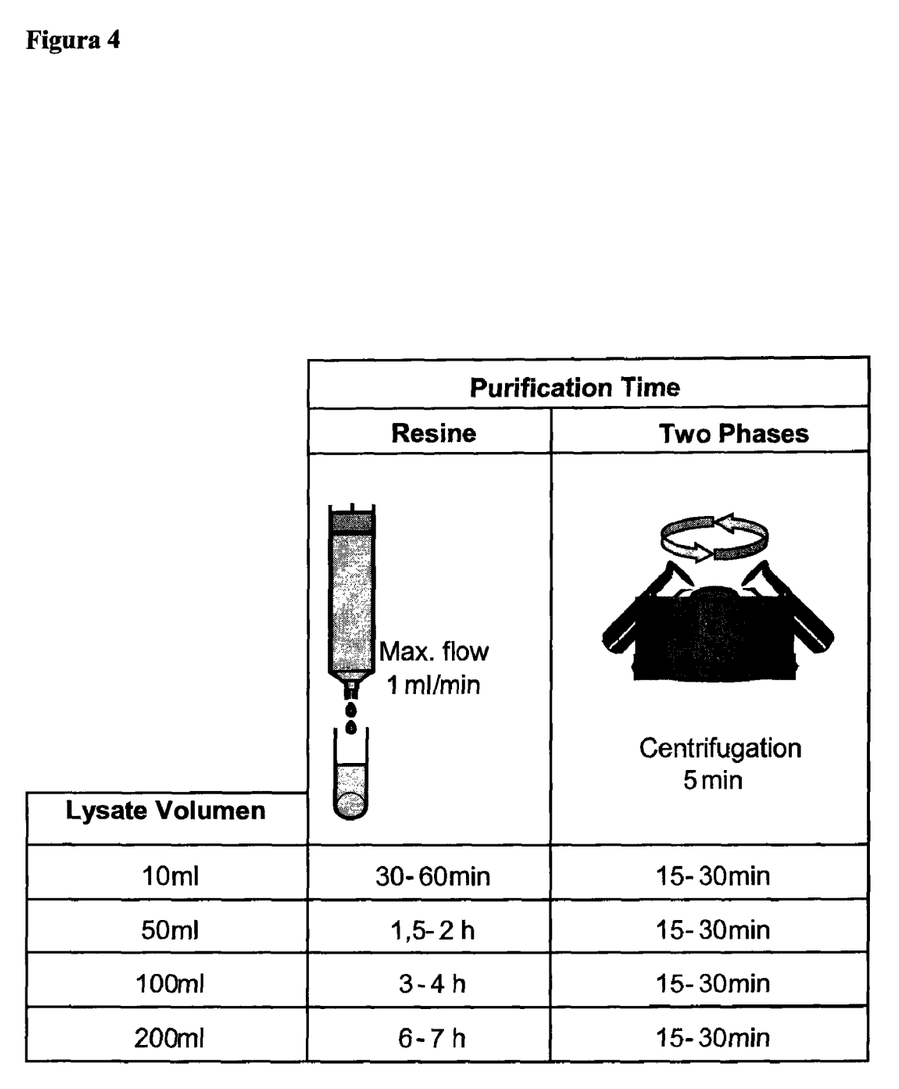
FIG. 4. Comparative diagram of the purification by affinity partitioning in two-phase aqueous systems and by affinity chromatography in a solid support.

The described invention presents several advantages over other existing protein purification systems, such as being a simple, fast and economic procedure that allows purification in mild conditions. The versatility of the system is based on the wide range of reagents and reagent concentrations that can be used, allowing the adjustment to the specific needs for each particular case. Furthermore, the system is free of technical problems associated with column chromatography, such as the need for packing, pressure and clogging issues, etc., and is faster and more easily scalable than those using solid supports (FIG. 4). In addition, the absence of toxic components (such as heavy metals in the case of the systems based on the hexahistidine "tag") makes the LYTAG two-phase an environment-friendly procedure. In the described system, the absorption of the protein to the affinity compound takes place in solution, and therefore in a more efficient manner than with affinity supports based on surfaces, such as the chromatographic resins. Furthermore, the interaction of the CBM LYTAG with PEG induces stabilization of the protein in a wide pH range, opening the possibility of using these purification systems at pH values far from neutral, thus overcoming the existence of electrostatic repulsions between the protein and the chromatographic supports that takes place at acid pH values. In the examples studied, the dual affinity of the CBM for PEG and for choline seems to be the dominant criterion regarding partitioning of the LYTAG-fused protein, driving the location of a given fusion protein to the desired phase by simply adding or omitting choline from the system. Although in general it seems that the PEG/phosphate and PEG/dextran systems are a priori suitable for the affinity partitioning of proteins fused to CBMs as LYTAG, different features in the protein of interest, such as overall charge, size and hydrophobicity, will influence the performance of each system and hence the choice of one over the other. In this sense, the present invention is very versatile, as there are different parameters to act on for adapting the system to each particular fusion protein in order to improve partitioning, namely ionic force, temperature, pH and use of detergents, among others (Johansson, H. W. a. G., ed. *Aqueous Two-Phase Systems. Methods in Enzymology*. Vol. 228. 1994). Furthermore, the present invention contemplates the potential use of alternative two-phase systems such as PEG/citrate, PEG/sulphate and PEG/starch. In the case of poorly soluble proteins, extraction can be carried out in large buffer volumes, thus diluting the sample and minimizing protein aggregation and precipitation. Finally, the procedure can be integrated in enzymatic processes of biotransformation in which the enzyme can be confined in one phase or the other at will (by omitting or adding choline), while the products accumulate in the opposite phase, facilitating this way the purification of the products, minimizing the possible incidence of enzymatic inhibition by product, and recycling of the catalyst.

FIGURES DESCRIPTION

FIGURES DESCRIPTION

FIG. 1. Purification of fusionated proteins to LYTAG through partition by affinity.

FIG. 2. CD analysis in the far ultraviolet of the pH effect in the LYTAG structure at 20° C. (A), wavelength spectra registered at pH 7.0 (filled symbols) and pH 5 (opened symbols) in absence of additives (circles), in presence of 10% PEG (triangles) or in presence of choline 140 mM. (B), titration of pH followed by the CD signal at 223 nm in absence of additives (filled circles), in presence of choline 140 mM (squares) and in presence of 10% PEG (open circles).

FIG. 3. Thermal stability of LYTAG followed by circular dichroism in absence of additives (o), in presence of PEG 10% (●) and presence of choline 150 mM (x).

FIG. 4. Comparative diagram of the purification systems in two aqueous phases and by affinity chromatography.

FIG. 5. Distribution of the protein GFP-LYTAG in the systems of two phases PEG/dextran (tube on the left) and PEG/phosphate (tube on the right), before (A) and after (B) of the elution with WashD+choline and WashP+choline buffers, respectively. C), SDS-PAGE of the fraction coming from the purification in PEG/phosphate. Street 1, Crude extract of REG-1 [pALEX2-Ca-GFP]; Street 2, Molecular weight patron; Street 3, Pure protein control, obtained by affinity chromatography; Street 4, Upper phase before the elution, rich in PEG; Street 5.—Lower phase before the elution, rich in phosphate; Street 6.—Upper phase after the elution; Street 7, Lower phase after the elution.

FIG. 6. SDS-PAGE of the fractions coming from the LYTAG-Protein A purification in PEG/dextran. (A) Street 1, Molecular weight patron; Street 2, Crude extract of REG-1 [pX]; Street 3, Upper phase before washings, rich in PEG; Street 4.—Lower phase before washings, rich in dextran; Street 5.—Upper phase after the first washing; Street 6, Lower phase after the first washing; Street 7, Upper phase after the second washing; Street 8, Lower phase after the second washing. (B), Street 1, Molecular weight patron, Street 2, Upper phase after the first elution; Street 3, Lower phase after the first elution; Street 4, Upper phase after the second elution; Street 5, Lower phase after the second elution. (C), SDS-PAGE of the fractions coming from the purification in PEG/phosphate. Street 1, Molecular weight patron; Street 2, Crude extract of REG-1 [pX]; Street 3, Upper phase before elution, rich in PEG; Street 4.—Lower phase before elution, rich in phosphate; Street 5.—Upper phase after elution; Street 6, Lower phase after elution.

REALIZATION EXAMPLES OF THE INVENTION

Example 1

Purification of a LYTAG-GFP Fusion

Figure 5:
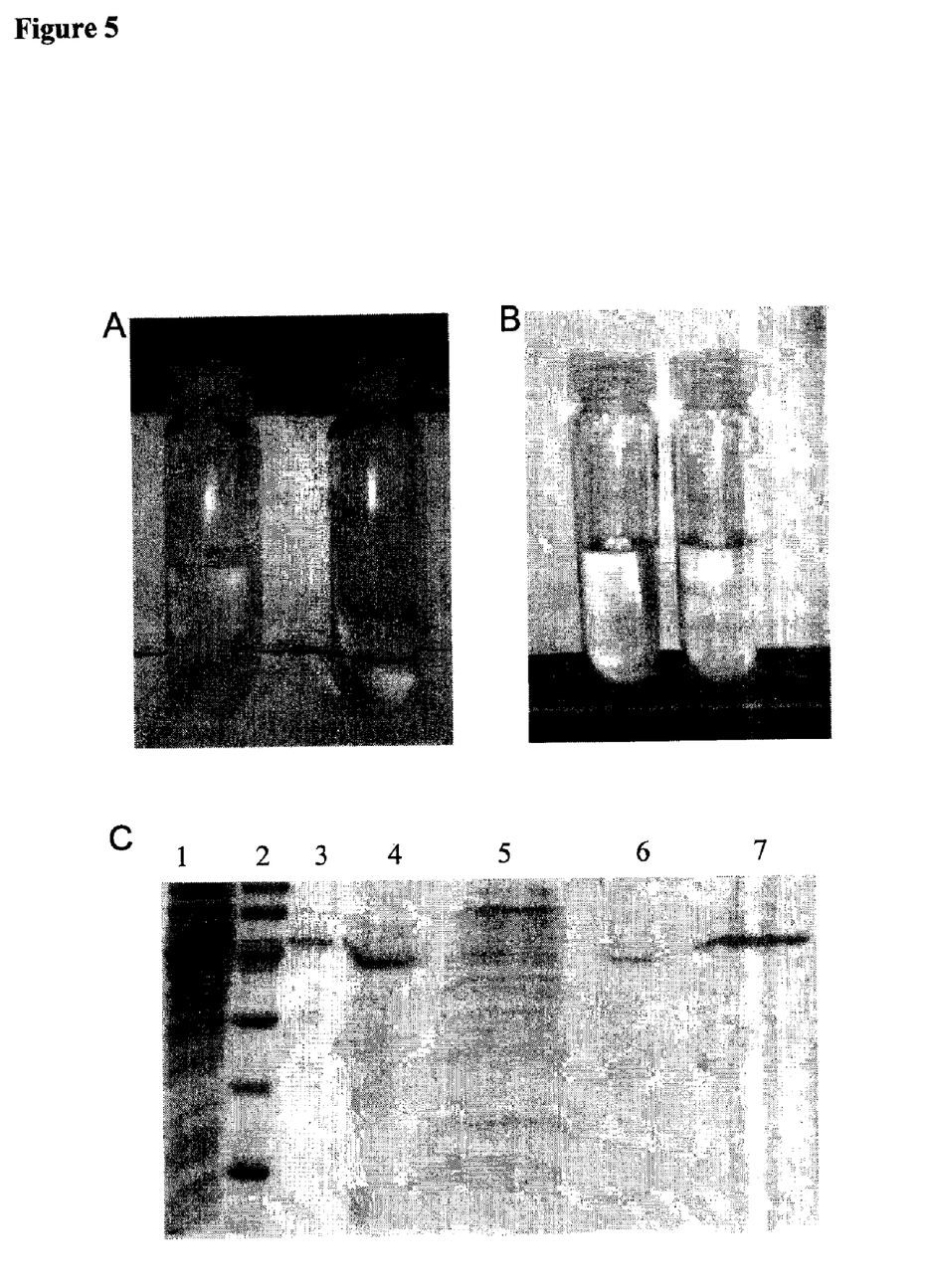
FIG. 5. Partitioning of the GFP-LYTAG protein in the two-phase aqueous systems PEG/dextran (left tube) and PEG/phosphate (right tube), before (A) and after (B) elution with WashD+choline and WashP+choline buffers, respectively. C), SDS-PAGE of the fraction coming from the purification in opposite phase, facilitating its purification and minimizing the risks of enzymatic inhibition by product.

The present example shows how can be done the purification of a fusion of a fluorescent protein to a CBD domain, concretely the LYTAG. For this realization example of the invention, the expression of the fusion to the green fluorescent GFP-LYTAG protein is carried out from 400 ml of a culture of the *E. coli* REG-1 strain (Biomedal, Espana, www.biomedal.com) transformed with the plasmid of pALEX2-Ca-GFP expression, obtained from the pALEX2-Ca vector (Biomedal), being incubated said culture at 37° C. until the expression induction of the GFP-LYTAG protein through the addition of salicylate to the medium, according to the recommendations from the "kit" LYTAG of Biomedal. The cells are collected by centrifugation and they are resuspended in 20 ml of 20 mM potassium phosphate buffer pH 8.0 in the case that the purification is carried out in the PEG/Phosphate system, or in Tris-HCl 20 mM pH 8.0 in the case of the PEG/Dextran system. After the cell lysate by sonication and the centrifugation for removing the cellular rests, to each aliquot is added by weighted the needed quantity of PEG, potassium phosphate or dextran for reconstituting the ExtP and ExtD buffers aforementioned. The solution is mildly agitated (with the object to reduce the DNA fragmentation and its presence as contaminant in the protein final preparation), in a beaker until the total resuspension of both compounds, and it is centrifuged during 5 minutes at 12.000 rpm and room temperature (for more sensitive proteins at temperature it is also possible to centrifugate at 4° C.). The specific affinity proved of the "tag" LYTAG by the PEG determines that in the two tested cases it is produced a fusion protein accumulation in the rich phase in PEG (upper phase) (FIG. 5A). The green colour of the upper phase, in which is found the GFP-LYTAG protein confirms that it is found perfectly folded and it is functional. In the lower phase, rich in phosphate and dextran, it remains the majority of cell proteins, it makes possible that the purity grade of the GFP-LYTAG fusion in the upper phase is already quite high (FIG. 5C). In any case, the choline addition to the Wash buffers causes the GFP-LYTAG protein elution to the lower phase (FIGS. 5B and 5C). There is to make notice, firstly, that the electrophoretic gels presented in these figures show an anomalous mobility of the proteins, due to the interference of the high salt concentrations and polymers used. Although the protein elution is not total in a first extraction (FIG. 5C, street 6), successive extractions through the addition of new fresh lower phase containing choline, allow to recover the major part of the GFP-LYTAG fusion present in the system (data not showed). It can be checked that, for this concret protein, the PEG/phosphate system provides a yield (around to 5 mg by liter of culture) and a purity grade slightly high than the achieved with the PEG/Dextran system.

Example 2

Purification of a LYTAG-Protein A Fusion

Figure 6:
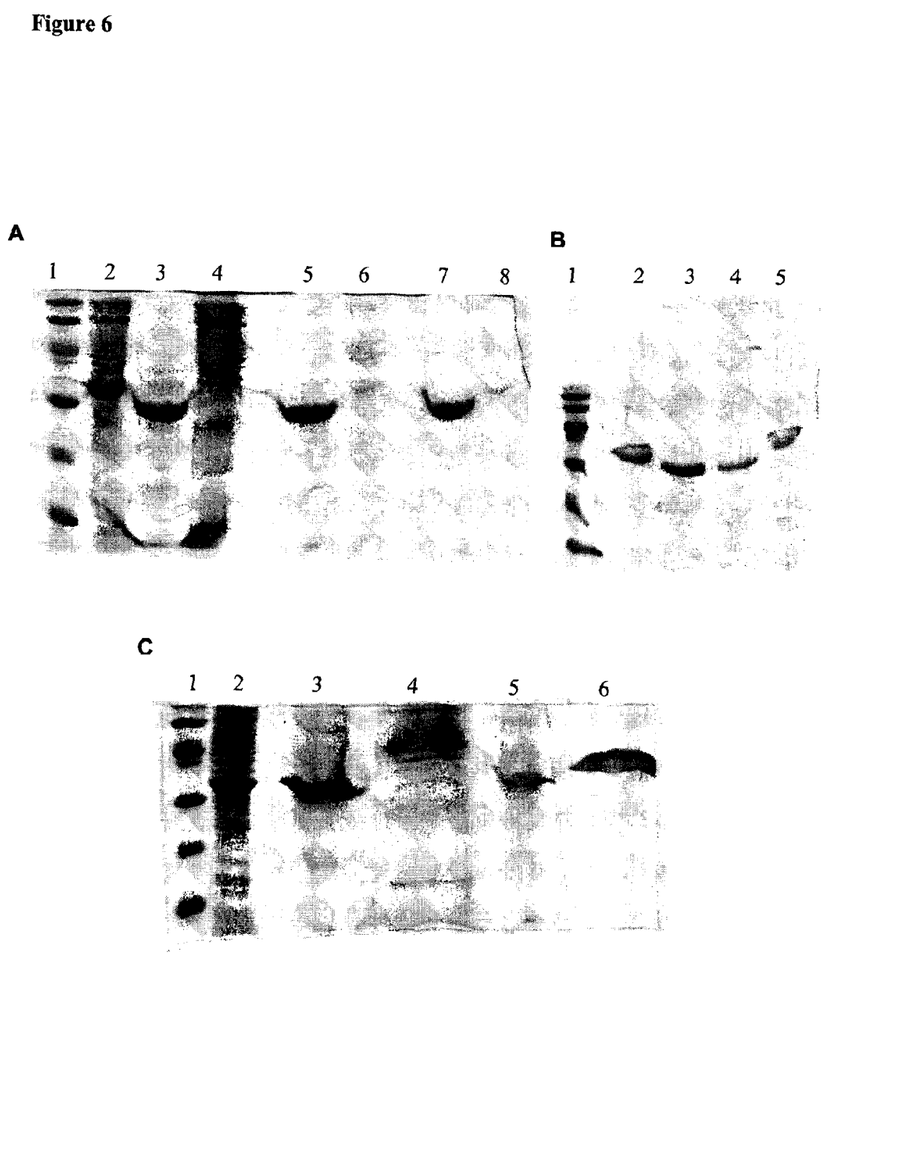

This example shows how through the present invention can be purified a fusion of a C-LytA choline-binding domain fusionated to a fragment of the protein A from *Staphylococcus aureus* which is bound to immunoglobulins. For this realization example is followed the same procedure that the described for the LYTAG-GFP fusion of the previous example, but being used a culture of the REG-1 strain transformed with the pALEXb-ProtA plasmid, built from the pALEXb vector (Biomedal), obtaining good purification using any of the two systems, as PEG/Dextran (FIGS. 6A and 6B) as PEG/Phosphate (FIG. 6C). As well as in the before case, the use of Dextran instead of Phosphate forces to increase the number of washing steps (two in this case). Again, after the washings, the protein LYTAG-protein A remains practically pure in the PEG phase. Likewise, the addition of fresh lower phase with choline allows the location of the polypeptidic fusion in the Dextran phase, recovering the basically all of the protein after several elution steps.

Example 3

Purification of a Fusion LYTAG-Lip36

Figure 7:
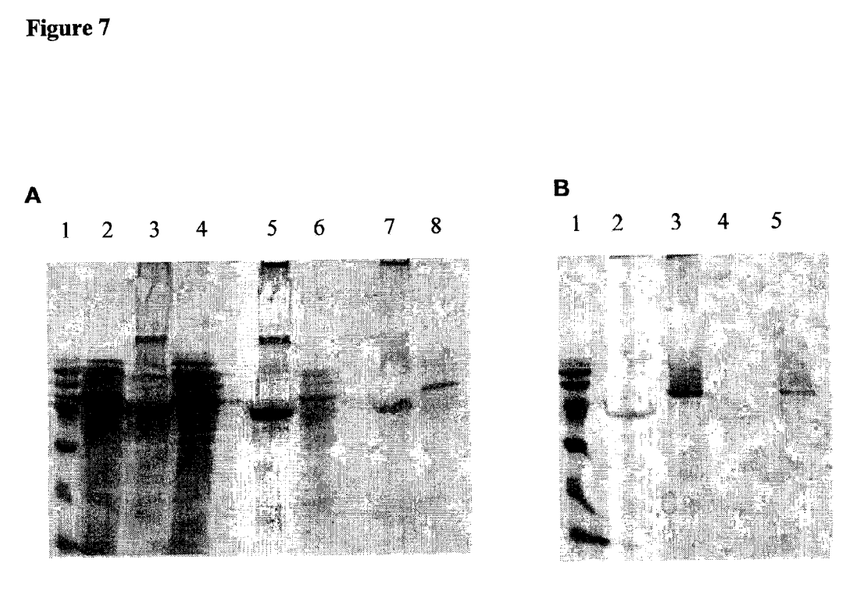
FIG. 7. SDS-PAGE of the fractions coming from the LYTAG-Lip36 purification in PEG/dextran. (A) Street 1, Molecular weight patron; Street 2, Crude extract of REG-1 [pALEXb-Lip36]; Street 3, Upper phase before washings, rich in PEG; Street 4.—Lower phase before washings, rich in dextran; Street 5.—Upper phase after the first washing; Street 6, Lower phase after the first washing. Street 7, Upper phase after the second washing. Street 8, Lower phase after the second washing. (B), Street 1, Molecular weight patron; Street 2, Upper phase after the first elution; Street 3, Lower phase after the first elution; Street 4, Upper phase after the second elution; Street 5, Lower phase after the second elution.

It is done as in the previous examples but from a culture of the strain REG-1 transformed with the pALEXb-Lip36 plasmid, built from the pALEXb vector (Biomedal). In this case the purification only results effective in the PEG/dextran system. The FIG. 7 shows, again, that it is needed several washings when it is used this polymeric par. The yields oscillate between 5-10 mg per litre of culture.

Example 4

Purification of a LYTAG-B-Galactosidase Fusion

Figure 8:
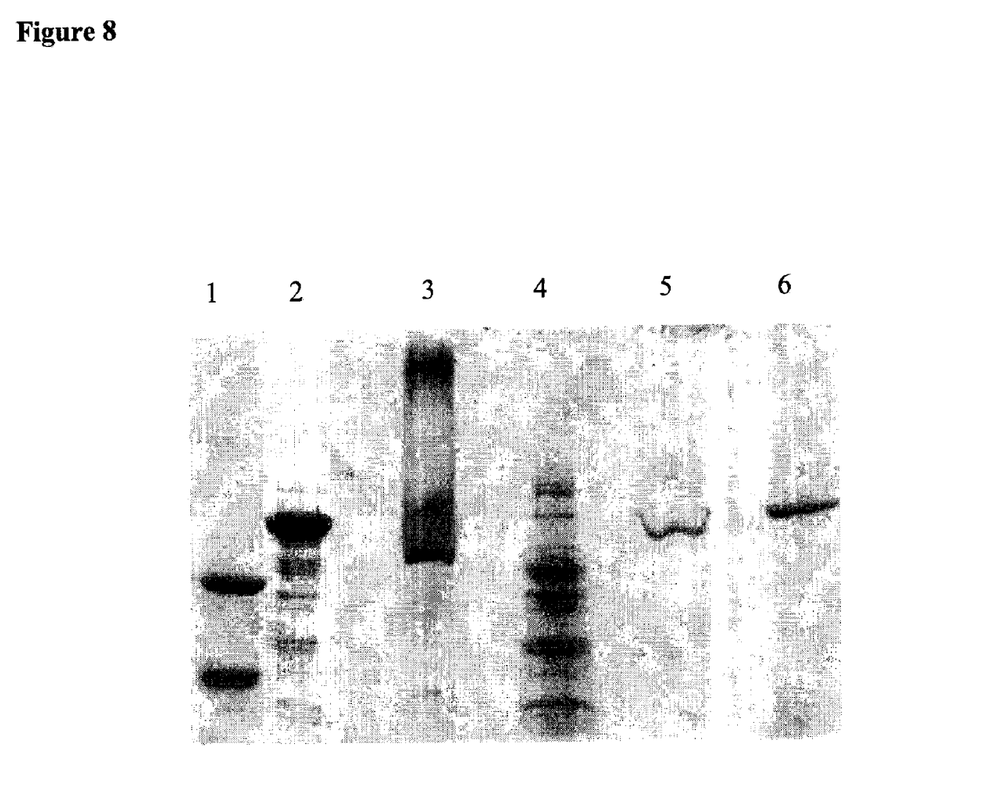
FIG. 8. SDS-PAGE of the fractions coming from the LYTAG-B-galactosidase purification in PEG/dextran. Street 1, Molecular weight patron; Street 2, Crude extract of REG-1 [pALEX2c-LacZ]; Street 3, Upper phase before washings, rich in PEG; Street 4.—Lower phase before washings, rich in dextran; Street 5.—Upper phase after the first washing; Street 6, Lower phase after the first elution.

In this example, carried out in a similar way than the previous but using a fusion LYTAG-B-galactosidase expressed from a culture of the strain REG-1 transformed with the pALEX2c-LacZ plasmid, built from the pALEX2c vector (Biomedal), it is proved the capacity of the partition system in two phases for the purification of a high molecular weight protein and oligomeric as is the beta-galactosidase. In this case, it could be the possibility of that the biophysical characteristics of the fusionated part to LYTAG dominate over the choline-binding module as for the protein tendency to be located in one or another phase. In this sense, it can be checked certain protein losing in the interphases, probably due to the big size of the fusion. Despite it, the hybrid protein can be purified with an acceptable purity grade in the PEG/dextran system, as it is showed in the FIG. 8. The protein thus purified preserves its activity in front of synthetic substrates as the o-1 2 3 4 5 6 nitrophenylgalactopyranoside (ONPG) (data not showed), indicating its structural stability and adequate folding as in the case of the fusion GFP-LYTAG described in the example 1.

Example 5

Purification of Fusionated Proteins to LYTAG Secreted into the Culture Medium

In this case, the present invention can be used for the purification of recombinant proteins secreted into the culture medium, either to bacteria, as for yeasts and other microorganisms. The yeast *Pichia pastoris* has an effective secretion machinary, quality that is taken advantage to the production of proteins of interest fusionated to a leader peptide that directs its transport towards the extracellular medium, through, for example, the use of the pPIC9 vector (*Pichia* Expression Kit, Invitrogen). If this protein is fusionated, moreover, to the choline-binding domain LYTAG, as it happens in the pPIC9-CLYT vector (Caubin, J., et al., Choline-binding domain as a novel affinity tag for purification of fusion proteins produced in *Pichia pastoris*. Biotechnol Bioeng, 2001. 74(2): p. 164-71), it can be purificated from the extracellular medium through one of the aqueous two-phase systems described. For it, a transformant of the strain GS115 of *P. pastoris* transformed with a construction derived of the pPIC9-CLYT plasmid and that express a secretable fusion of LYTAG to the protein of interest, it can be cultivated in BMGY buffered medium at 30° C. until reach a $DO_{600}$ of 2-6, moment in which it is induced the expression of the fusion to LYTAG changing the carbone source, from glycerol 1% (BMGY medium) to methanol 0.5% (BMMY medium). After 15-24 hours of induction, it is centrifuged the culture and it is recuperated the supernatant. This supernatant, which contains the fusion protein to secreted LYTAG can thus be directly submitted to one of the purification systems described in the previous examples, leading this process to the purification of the protein of interest.

Likewise, the purification of proteins fusionated to choline-binding domains from the culture medium, can also be done from bacterial cultures of *E. coli* that express fusions LYTAG-protein or protein-LYTAG to leader peptides that conduct the transport of the fusion towards the periplasmic space or towards the extracellular medium.

Example 6

Purification of Antibodies in Two Phases Through the Use of LYTAG Protein A

The protein A shows affinity by immunoglobulins, characteristic that can be used for the antibodies purification through the two-phase systems described in the example 2. In the present example, it can be dissolved the two-phase components in a mixture of 1 ml of LYTAG-Protein A (5-10 mg/ml) purified and dialized in 20 mM phosphate buffer pH 8.0 (in the case that it is going to use the system PEG/dextran), and 19 ml of supernatant of the hybridome culture that express the antibody of interest. The supernatant must be dialized in 20 mM phosphate buffer pH 8.0 (in the case that it is going to use the system PEG/phosphate), or in 20 mM Tris-HCl buffer pH 8.0 (in the case that it be used the system PEG/dextran). Once dissolved the two compounds it is preceded to the separation, washing and elution in the described conditions for the previous examples, being able to give rise finally to the obtaining in the lower phase of protein A-antibody complexes with a high purity grade. Alternatively, the antibodies can be recuperated purified through the use in the last step of pH conditions and ionic force that favouring their separation of the fusion LYTAG-Protein A, which it would be retained in the phase rich in PEG and could be re-used.

The invention claimed is:

1. A method for partitioning or separating proteins or polypeptides linked to choline binding polypeptides characterized by:
   a) contacting
      i) a crude or partially purified extract of a cell culture, or the extracellular medium of a cell culture, or a mixture of different chemical compounds containing at least one protein or polypeptide whose sequence has at least one choline-binding structural motif,
      ii) with a mixture of water, polyethylenglicol (PEG) and salts or other polymers more than 5% soluble in water, the resulting mixture being spontaneously structured into a binary system with two aqueous phases, A and B, phase A being richer in PEG than phase B, and wherein proteins or polypeptides with said choline-binding motifs partition preferentially to phase A b) optionally suppressing the preferential partitioning of said proteins or polypeptides containing the choline binding motifs to phase A, by adding a solution containing choline.

2. The method according to claim 1 characterized in that the total PEG concentration in the binary system is comprised between 3 and 15%.

3. The method according to claim 1, characterized in that the salt present in the phase B of the binary system is selected between a phosphate, citrate, sulphate salt or a mixture thereof.

4. The method according to claim 1, characterized in that the salt present in the phase B of the binary system contains potassium phosphate at a concentration comprised between 5 and 15%, and the pH of the mixture has a value comprised between 6.0 and 9.0.

5. The method according to claim 1, characterized in that the polymer present in the phase B of the binary system is dextran or a dextran derivative at a concentration comprised between 5 and 10% and the pH of the mixture has a value comprised between 6.0 and 9.0.

6. The method according to claim 1, characterized in that the polymer present in the phase B of the binary system is starch or a starch derivative at a concentration comprised between 5 and 10% and the pH of the mixture has a value comprised between 6.0 and 9.0.

7. The method according to claim 1, characterized in that the polypeptidic sequence with affinity to choline derives from the C-terminal domain of the LytA amidase of *Streptococcus pneumoniae*.

8. The method according to claim 1, characterized in that the cell extract or the extracellular medium of the cellular culture originate from hybridomes, fungi, yeast or bacteria.

9. The method according to claim 1, characterized in that it comprises a further step consisting of the partial removal of the proteins from the cell extract or the extracellular culture medium that do not partition preferentially to phase A, by discarding phase B.

10. The method according to claim 9, characterized in that the proteins that do not partition preferentially to phase A are quantitatively eliminated through the following steps:
   i) adding an amount of solution equivalent in composition and volume to those of the phase B discarded,
   ii) mixing and separation in two phases, A and B
   iii) discarding the newly formed phase B; and
   iv) optionally repeating the previous steps.

11. The method according to claim 1, characterized in that the PEG-rich phase A containing the fusion protein or fusion polypeptide is used directly to obtain said fusion protein or fusion polypeptide in purified form.

12. A method for the partitioning or separation of fusion proteins or fusion polypeptides according to claim 1 comprising providing the C-terminal domain of the LytA amidase of *Streptococcus pneumoniae* as the sequence with affinity to choline.

13. Kit to perform the procedure for partitioning or separation of fusion proteins or fusion polypeptides according to claim 1, which comprises the following components:
   i) an aqueous solution with a PEG concentration between 3 and 15%;
   ii) an aqueous solution comprising a phosphate, citrate or sulphate salt or a mixture thereof, or dextran or starch; and
   iii) choline as a solid salt or in aqueous solution.

* * * * *